United States Patent
Zimmermann

(10) Patent No.: US 10,254,209 B2
(45) Date of Patent: Apr. 9, 2019

(54) SYSTEM AND METHOD FOR DETECTING PARTICLES

(71) Applicant: COMMISSARIAT A L'ENERGIE ATOMIQUE ET AUX ENERGIES ALTERNATIVES, Paris (FR)

(72) Inventor: Eric Zimmermann, Vif (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/510,778

(22) PCT Filed: Sep. 17, 2015

(86) PCT No.: PCT/EP2015/071293
§ 371 (c)(1),
(2) Date: Mar. 13, 2017

(87) PCT Pub. No.: WO2016/042060
PCT Pub. Date: Mar. 24, 2016

(65) Prior Publication Data
US 2017/0276590 A1  Sep. 28, 2017

(30) Foreign Application Priority Data
Sep. 18, 2014 (FR) ..................... 14 58809

(51) Int. Cl.
*G01N 21/00* (2006.01)
*G01N 15/06* (2006.01)
(Continued)

(52) U.S. Cl.
CPC ............. *G01N 15/065* (2013.01); *G01N 1/22* (2013.01); *G01N 15/0266* (2013.01);
(Continued)

(58) Field of Classification Search
CPC .. G01N 15/065; G01N 15/10; G01N 15/1459; G01N 1/22; G08B 21/12
(Continued)

(56) References Cited

U.S. PATENT DOCUMENTS 5,027,642 A * 7/1991 Wen .................. F17C 7/00
324/71.4
2007/0242261 A1* 10/2007 Liu ..................... G01N 1/2252
356/37
(Continued)

OTHER PUBLICATIONS

International Search Report dated Nov. 24, 2015 in PCT/EP2015/071293 filed Sep. 17, 2015.
(Continued)

*Primary Examiner* — Sunghee Y Gray
(74) *Attorney, Agent, or Firm* — Oblon, McClelland, Maier & Neustadt, L.L.P.

(57) ABSTRACT

A system for detecting particles, including: a first device to measure concentration of particles, including an electrometer measuring device coupled to a charger and/or to an optical particle counter; a second device to measure concentration of particles, including a condensation nuclei counter; a calculation unit configured to calculate a ratio and/or a difference between a first measurement of the particle concentration in an airflow, to be performed by the first measurement device, and a second measurement of the particle concentration in an airflow, to be performed by the second measurement device, and configured to provide a comparison between the ratio and/or the difference between the first and second measurements and a threshold value to determine presence of particles of interest other than ambient air particles.

21 Claims, 10 Drawing Sheets

(51) Int. Cl.
  *G01N 15/02* (2006.01)
  *G01N 1/22* (2006.01)
  *G01N 15/10* (2006.01)
  *G01N 15/14* (2006.01)
  *G08B 21/12* (2006.01)
  *G01N 15/00* (2006.01)

(52) U.S. Cl.
  CPC ......... *G01N 15/10* (2013.01); *G01N 15/1459* (2013.01); *G08B 21/12* (2013.01); *G01N 1/2211* (2013.01); *G01N 2015/0038* (2013.01)

(58) Field of Classification Search
  USPC ........................................................ 356/338
  See application file for complete search history.

(56) References Cited

U.S. PATENT DOCUMENTS

2009/0064760 A1\* 3/2009 Moriya ................ G01N 1/2202
  73/28.04
2011/0056273 A1\* 3/2011 Gorbunov ............ G01N 15/065
  73/28.01

OTHER PUBLICATIONS

French Search Report dated May 13, 2015 in FR1458809 filed Sep. 18, 2014.
Biermann, A.H. et al., "Filter Penetration Measurements Using a Condensation Nuclei Counter and an Aerosol Photometer," Journal of Aerosol Science, vol. 19, No. 4, Aug. 1, 1988, pp. 471-483, XP055189008.
Kuwata, M. et al., "Dependence of CCN Activity of Less Volatile Particles on the Amount of Coating Observed in Tokyo," Journal of Geophysical Research, vol. 112, Jun. 7, 2007, pp. 1-9, XP019943759.
Park, Mikyung et al., "Development of a cloud condensation nuclei (CCN) counter using a laser and charge-coupled device (CCD) camera," Front. Environ. Sci. Engin. China., vol. 5, No. 3, Jul. 2011, pp. 313-319, XP055189010.

\* cited by examiner

SYSTEM AND METHOD FOR DETECTING PARTICLES

TECHNICAL DOMAIN AND PRIOR ART

The invention relates to the domain of detection of particles or aerosols, and particularly nanoparticles or nanometric aerosols. The invention is advantageously applicable to the field of monitoring and checking the presence of particles in an atmosphere, for example for monitoring the exposure of persons to aerosols.

Particles may be detected by different types of particle concentration measurement devices each based on a particular measurement type: optical, electrical, etc.

A particle concentration measurement can be carried out using a condensation nuclei counter, or Condensation Particle Counter (CPC). In such a device, an air flow to be characterised is directed into a vapour saturation zone and then into a vapour condensation zone so as to condense the vaporised liquid around particles contained in the air flow and increase the size of these particles sufficiently to make them optically detectable. The condensation particle counter then counts these particles individually or by attenuation and thus measures a concentration as a number of particles contained in the air flow.

A particle concentration measurement can also be carried out using an electrometer measuring device. Such a measurement device is coupled to an element called a "charger" that has the function of electrically charging particles by depositing electrical charges on the particle surface. In this case, an electrical potential difference is applied between two zones of the charger so as to generate electrical charges in the air flow to be characterised and these charges are deposited on the particles, for example using a nail, a needle and a charger wall by the corona effect. The electrometer measuring device that receives the air flow containing electrically charged particles, comprises one or several electrometers that collect electrical charges deposited on the surface of particles. The current induced by the collected electrical charges is then processed in a measurement chain to estimate a concentration and possibly a size grading distribution of particles (in other words different particle concentrations depending on their size).

However, several problems arise with these particle concentration measurement devices.

Firstly, these devices that make measurements in real time (result obtained for example after a time of less than about 1 minute) or quasi-real time (result obtained for example after a time of less than about 1 hour) are not sensitive to the chemistry of particles. This creates a major difficulty because ambient air can contain a large and highly variable quantity of particles that form a background noise additional to the particles of interest that are to be detected (for example manufactured nanoparticles). Since these devices cannot distinguish between background noise and particles of interest, it is impossible to make such a measurement in real time or quasi-real time in the presence of a large background noise because measurement of the concentration of particle of interest involves a subsequent chemical analysis to identify particles of interest among the various particles detected.

There are proven analysis methods for determining the chemical nature of aerosols, particularly after particles have been selected by size. These methods are capable of determining a concentration of particles of interest, even in the presence of a background noise. However, these analyses require sampling and a subsequent characterisation of these samples. Therefore such methods are not suitable for particle detection in real time or in quasi-real time.

Moreover, particles of interest other than particles in ambient air, for example manufactured nanoparticles, that are to be detected tend to coalesce into groups and form particle aggregates or clusters. However, a condensation particle counter does not make a distinction between a single particle and an aggregate or cluster of particles during counting. Therefore the measurement of a particle concentration carried out by a CPC for detecting particles of interest other than natural particles in ambient air is not representative of the real number of individual particles. Furthermore, these aggregates or clusters of particles have a high specific surface area that can hold many electrical charges, which causes a strong response of an electrometer measuring device during detection of such particles. Therefore the result of the measurement of a particle concentration carried out with an electrometer measuring device is also not correct in the presence of aggregates or clusters of particles of interest and is overestimated compared to the number of aggregates or clusters.

PRESENTATION OF THE INVENTION

One purpose of this invention is to disclose a system for detecting particles of interest that can be used to detect these particles in real or quasi-real time that is efficient even in the presence of a large and variable background noise, in other words in the presence of many particles in ambient air, and that does not require an analysis of the chemical nature of sampled particles after the measurement, and for which detection is not affected by the formation of aggregates or clusters of particles to be detected.

For this purpose, the invention discloses a particle detection system comprising at least:
- a first particle concentration measurement device comprising at least one electrometer measuring device coupled to a charger and/or comprising at least one optical particle counter;
- a second particle concentration measurement device, comprising at least one condensation particle counter;
- a calculation unit capable of calculating a ratio and/or a difference between a first measurement of the particle concentration in an airflow, intended to be performed by the first particle concentration measurement device, and a second measurement of the particle concentration in the airflow, intended to be performed by the second particle concentration measurement device.

Such a detection system judiciously combines two different particle concentration measurement devices to make two particle concentration measurements in parallel based on different measurement techniques.

When the first measurement device comprises a charger (that electrically charges particles in the air flow) coupled to an electrometer measuring device, it overestimates the measured concentration of particles of interest (due to the formation of aggregates or clusters of these particles of interest) relative to the concentration measured by the condensation particles counter. Therefore, calculating the ratio and/or the difference between the two previous measurements makes it possible to correctly detect the presence of particles of interest, regardless of the level of the background noise, in other words regardless of the concentration of particles in ambient air or in the ambient atmosphere (or ambient aerosol).

When the first measurement device comprises an optical particle counter (OPC), specifically the particle detection system monitors the variation of masses of aerosols estimated by the optical particle counter in comparison with the variation of the total concentration (aerosols of interest+ background noise) given by the condensation particle counter. Aggregates and clusters of particles of interest represent a significant mass for a low concentration of aggregates or clusters of particles. Therefore, since the optical particle sensor is not sensitive or is only slightly sensitive to the background noise at low particle concentrations, the difference and/or the ratio between the two measurements makes it possible to correctly detect the presence of particles of interest, regardless of the level of the background noise, in other words regardless of the concentration of particles in ambient air or in the ambient atmosphere (or ambient aerosol).

Furthermore, the calculation of this ratio and/or this difference between particle concentration measurements avoids the need for a subsequent analysis of the chemical nature of the sampled particles. Therefore this detection system is capable of detecting the presence of particles of interest in an ambient atmosphere in real time or quasi-real time. The response time of the detection system may be less than a minute, or even of the order of a second.

The term "particles" is used in this context and in the remainder of this document to refer to nanoparticles (comprising at least one dimension smaller than about 100 nm), and slightly larger particles (dimensions smaller than one micron), and also refers to aggregates and/or clusters of such particles for which the dimensions can be equal to several microns.

The particle detection system may also comprise a flow separator comprising an inlet into which the air flow is intended to be directed and two outlets coupled to inlets to the first and second particle concentration measurement devices.

The particle detection system may also comprise a particle selection device located upstream from the flow separator and capable of selecting at least some of the particles in the air flow depending on their behaviour (electrical mobility and/or aerodynamic mobility and/or size) such that the air flow received by the first and second particle concentration measurement devices contains only the selected particles.

The particle selection device may comprise a cyclone, or the particle selection device may comprise an electrical mobility differential analyser coupled to a charger or an electrical charge neutraliser of particles in the air flow.

The calculation unit may be capable of making a comparison between the ratio and/or the difference between the first and second measurements of the concentration of particles in the air flow and a threshold value to determine the presence of particles of interest other than those in ambient air.

The particle detection system may also comprise a processing unit of the signal output by the calculation unit The particle detection system may also comprise a device capable of determining the nature of particles in the air flow.

The calculation unit may also be capable of calculating a concentration of particles of interest contained in the air flow and distinct from particles in ambient air.

The invention also relates to a method of detecting particles including at least the following steps:
a first measurement of a concentration of particles in an air flow by a first particle concentration measurement device comprising at least one electrometer measuring device coupled to a charger and/or comprising at least one optical particle counter;
a second measurement of a concentration of particles in the air flow by a second particle concentration measurement device comprising at least one condensation particle counter,
calculate a ratio and/or a difference between the first and the second measurements of the particle concentration in the air flow.

During the first measurement, when the first measurement device comprises the electrometer measuring device coupled to the charger, a step is carried out by the charger for electrically charging the particles in the air flow such that the first particle concentration measurement is carried out from the air flow containing the electrically charged particles.

The method may also include, before the first and second particle concentration measurements, a step to select at least some of the particles in the air flow as a function of their behaviour (electrical mobility and/or aerodynamic mobility and/or size), such that the first and second particle concentration measurements are carried out from the air flow that contains only the selected particles.

The method may also include, after the step to calculate the ratio and/or the difference between the first and second particle concentration measurements, a step to compare the ratio and/or the difference between the first and the second particle concentration measurements and a threshold value to determine the presence of particles of interest other than those in ambient air.

The method may also comprise a step to determine the nature of particles in the air flow.

The method may also include a step to calculate a concentration of particles of interest contained in the air flow and distinct from particles in ambient air.

BRIEF DESCRIPTION OF THE DRAWINGS

This invention will be better understood after reading the description of example embodiments given purely for information and in no way limitative with reference to the appended drawings on which.

Identical, similar or equivalent parts of the different figures described below have the same numeric references to facilitate the comparison between different figures.

The different parts shown on the figures are not necessarily all at the same scale, to make the figures more easily understandable.

The different possibilities (variants and embodiments) must be understood as not being mutually exclusive and can be combined with each other.

DETAILED PRESENTATION OF PARTICULAR EMBODIMENTS

Figure 1:
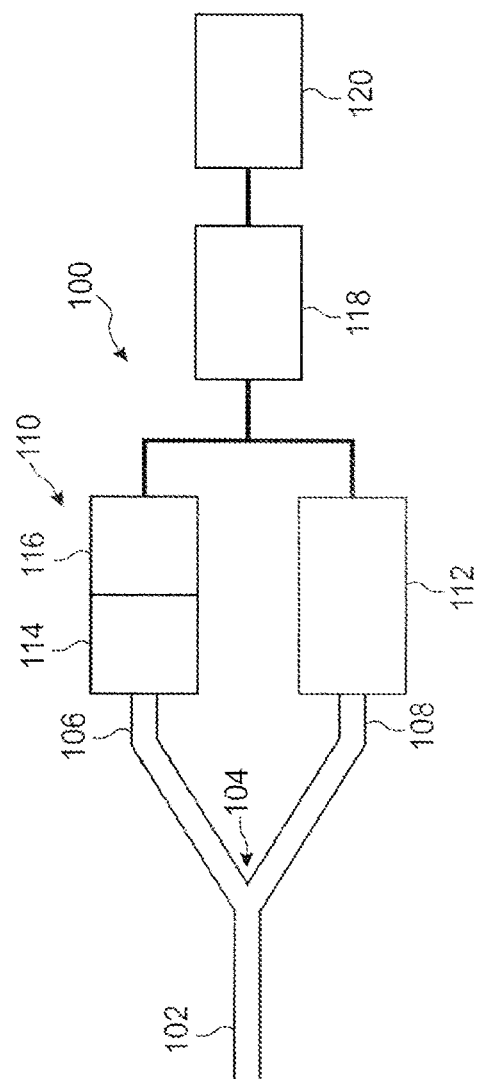
FIG. 1 diagrammatically shows a particle detection system according to a first embodiment of this invention.

Refer firstly to FIG. 1 that diagrammatically shows a first embodiment of a particle detection system 100.

The system 100 comprises an inlet channel 102 into which an air flow containing the aerosol to be characterised is sent, for example by suction. This air flow is then separated into two distinct flows by a flow separator 104 that is coupled to two other channels 106, 108 connected to the inlets of a first particle concentration measurement device 110 and a second particle concentration measurement device 112 respectively. The outlet of the channel 106 is connected to the inlet to a charger 114 of the first device 110. The charger 114 is capable of depositing electrical charges on the surface of particles in the received air flow. The first device 110 also comprises an electrometer measurement device 116, the inlet of which is coupled to the outlet from the charger 114. The second device 112 comprises a condensation particle counter (CPC). The channels 102, 106, 108 and the flow separator 104 are made so that they do not modify the aerosol to be characterised, particularly by maintaining the isokineticity of flows and by minimising particle deposits on the walls of these elements, for example by using an antistatic or stainless steel flow separator and channels.

Each of the two measurement devices 110, 112 makes a measurement of the concentration of particles in the air flow received by them. Data provided by these two devices 110, 112 are then sent to the input of a calculation unit 118, for example a computer or electronic calculation means, that calculates the ratio and/or the difference (the ratio in the example described herein) between the values of concentration measurements carried out by the two measurement devices 110, 112. The calculation unit 118 can also determine significant variations in the value of the ratio and/or this difference as it changes.

For a measurement of the particle concentration in an ambient air flow that does not contain any particles of interest that form aggregates and/or clusters of particles, the ratio of the concentration measurements carried out by these two measurement devices 110, 112 (in this case the ratio between the measurement made by the first device 110 and the measurement made by the second device 112) is close to 1, or is between about 0.5 and 2. On the other hand, for an air flow that also contains an aerosol of interest to be characterised, in other words also containing particles of interest other than those in ambient air and that do form aggregates and/or clusters of particles, the value of the particle concentration measured by the first device 110 is different from the value measured by the second device 112. The first device 110 provides a higher measurement value that that provided by the second measurement device 112 due to the aggregates and/or clusters of particles, the number of which is overestimated by the first device 110 due to the large number of electrical charges received by these aggregates and/or clusters of particles, and due to the fact that the second device 112 counts each of these aggregates and/or clusters as a single particle. Therefore an analysis of this difference in the measurements can demonstrate the presence of these particles of interest, different from those in ambient air that form a background noise, even if the concentration of particles in ambient air changes.

Figure 2:
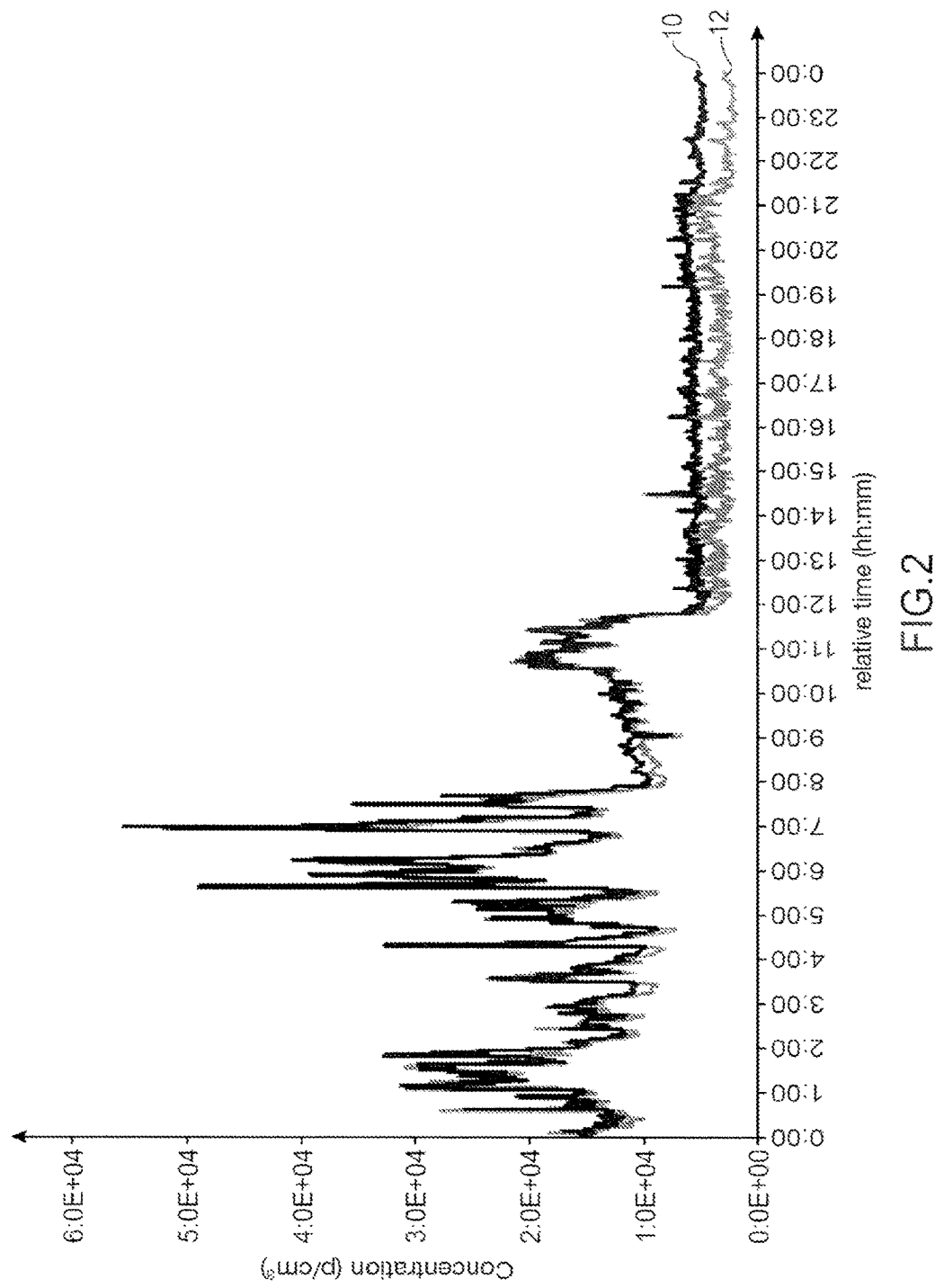
FIG. 2 shows measurements of ambient aerosol concentrations carried out by a particle detection system according to this invention.
Figure 3:
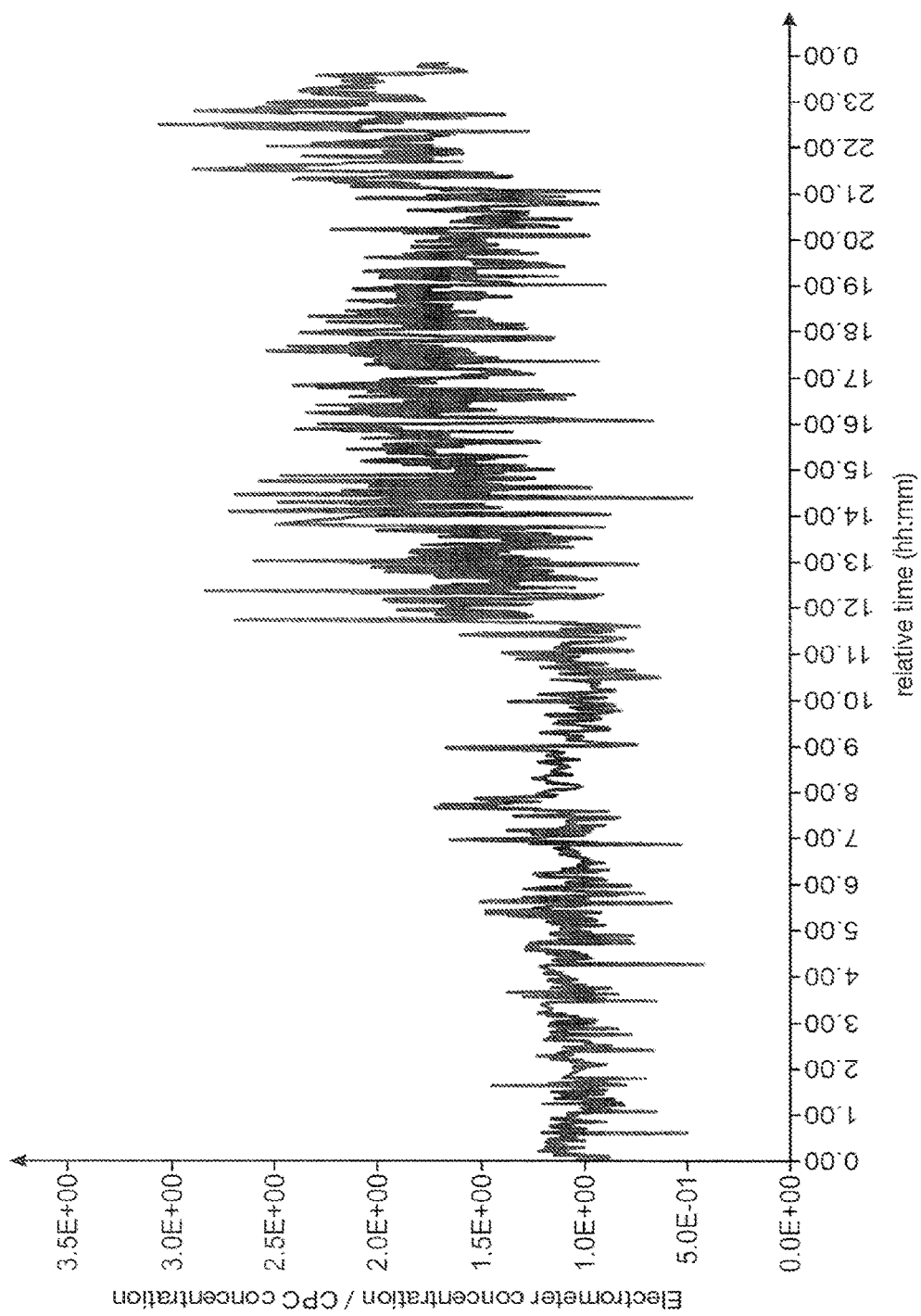
FIG. 3 shows the variation of the ratio of measurements of ambient aerosol concentrations calculated by the particle detection system according to this invention.

FIG. 2 shows the variation in particle concentrations (as the number of particles/cm$^3$) measured with the first device 110 (curve 10) and with the second device 112 (curve 12), over a 24-hour period, during a measurement of the concentration of particles in an ambient air flow that does not comprise particles of interest that form aggregates and/or clusters of particles. FIG. 3 shows the variation of the ratio between these measurements that is calculated by the calculation unit 118. These two FIGS. 2 and 3 clearly show that the two types of measurement device 110, 112 provide measurement results that almost identically follow variations in the concentration of particles in ambient air. For particle concentrations in ambient air that are mostly more than about 10000 particles/cm$^3$, the average value of the ratio between the two measurements is equal to about 1.07 and the associated standard deviation is about 0.16.

For particle concentrations in ambient air that are mostly less than about 10000 particles/cm$^3$, the average value of the ratio between the two measurements is equal to about 1.72 and the associated standard deviation is about 0.4.

Figure 4:
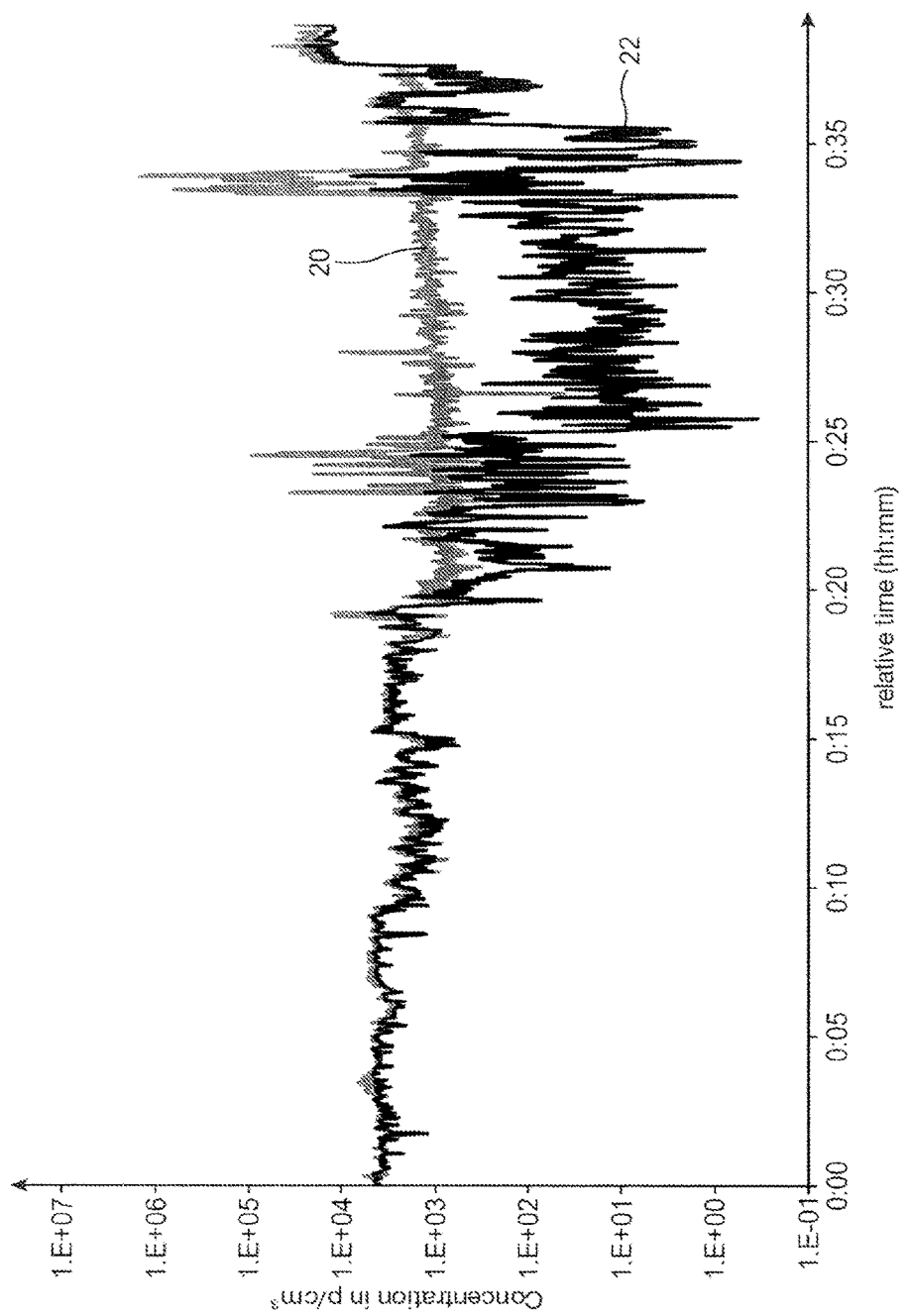
FIG. 4 shows measurements of particle concentrations in the presence of $TiO_2$ nanoparticles of interest carried out by the particle detection system according to this invention.
Figure 5:
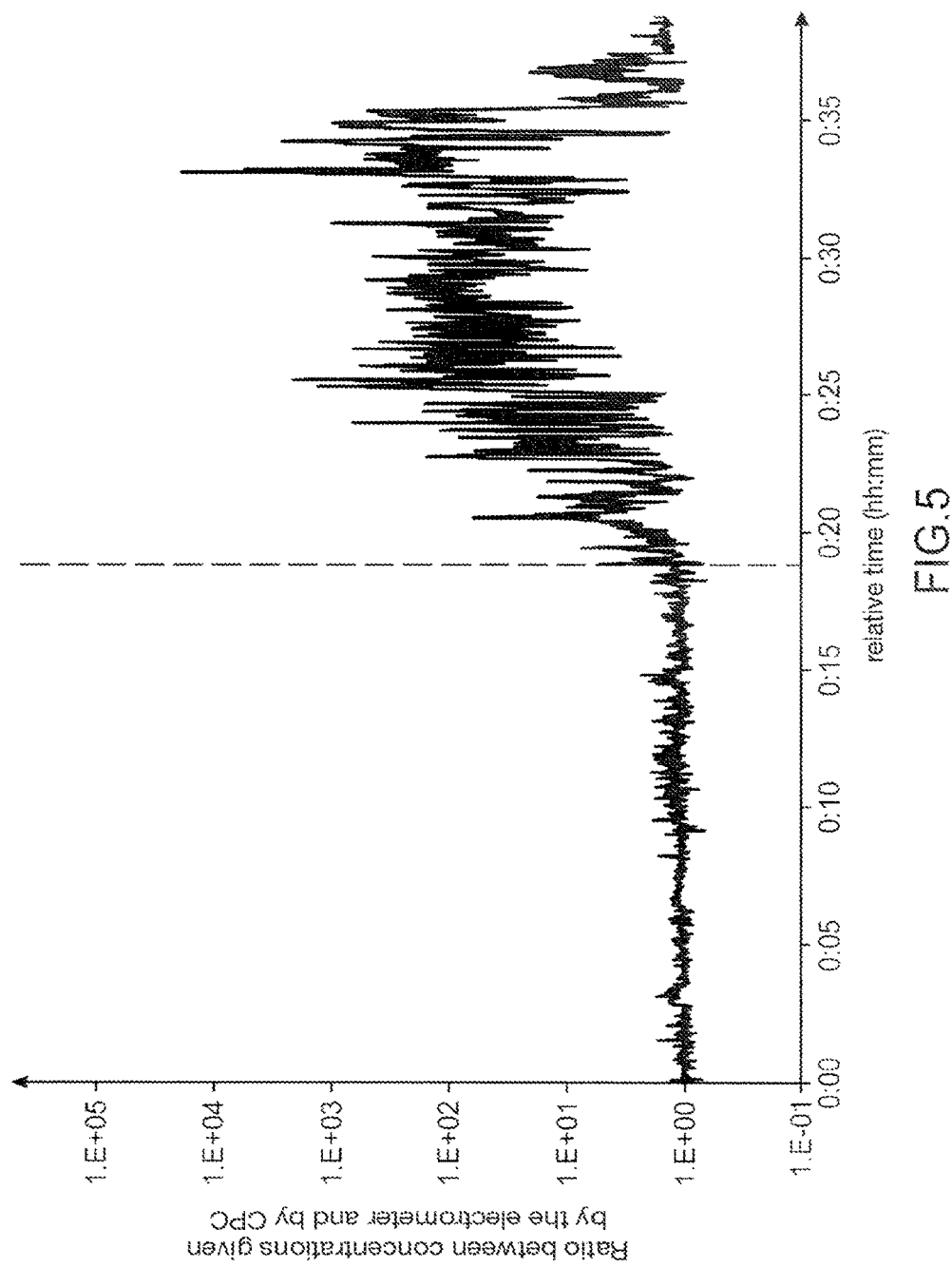
FIG. 5 shows the variation in the ratio between measurements of particle concentrations in the presence of $TiO_2$ nanoparticles of interest calculated by the particle detection system according to this invention.

FIG. 4 shows the variation in particle concentrations (as a number of particles/cm$^3$) obtained with the first device 110 (curve 20) and with the second device 112 (curve 22), over a 40-minute period, during a measurement of the concentration of particles in an air flow that comprises TiO$_2$ nanoparticles, in addition to particles in ambient air. These measurements are carried out during two phases: a first phase corresponding to the first 19 minutes during which the TiO$_2$ particles are not manipulated (that does not generate an aerosol of TiO$_2$ in the air flow), and a second phase from the 19$^{th}$ minute to the 40$^{th}$ minute during which the TiO$_2$ particles are manipulated (for example manipulations to take samples, make transfers, pouring, etc.) that does generate aerosols of TiO$_2$ in the air flow. FIG. 5 shows the variation of the ratio between these measurements that is calculated by the calculation unit 118. The ratio of concentrations is close to 1 as long as TiO$_2$ particles are not manipulated and therefore there are no TiO$_2$ aerosols in the air flow, as for the measurements described above with reference to FIGS. 2 and 3. As soon as TiO$_2$ particles are manipulated, thus generating TiO$_2$ aerosols in the air flow, the first device 110 strongly overestimates the concentration of particles in the air flow relative to the second device 112 due to the aggregates and/or clusters of TiO$_2$ particles that form. The ratio between measured concentrations quickly reaches 10 and at peaks even exceeds 10000 during the operation that causes the highest suspension of TiO$_2$ particles (between the 33$^{rd}$ and the 35$^{th}$ minute on these FIGS. 4 and 5).

Figure 6:
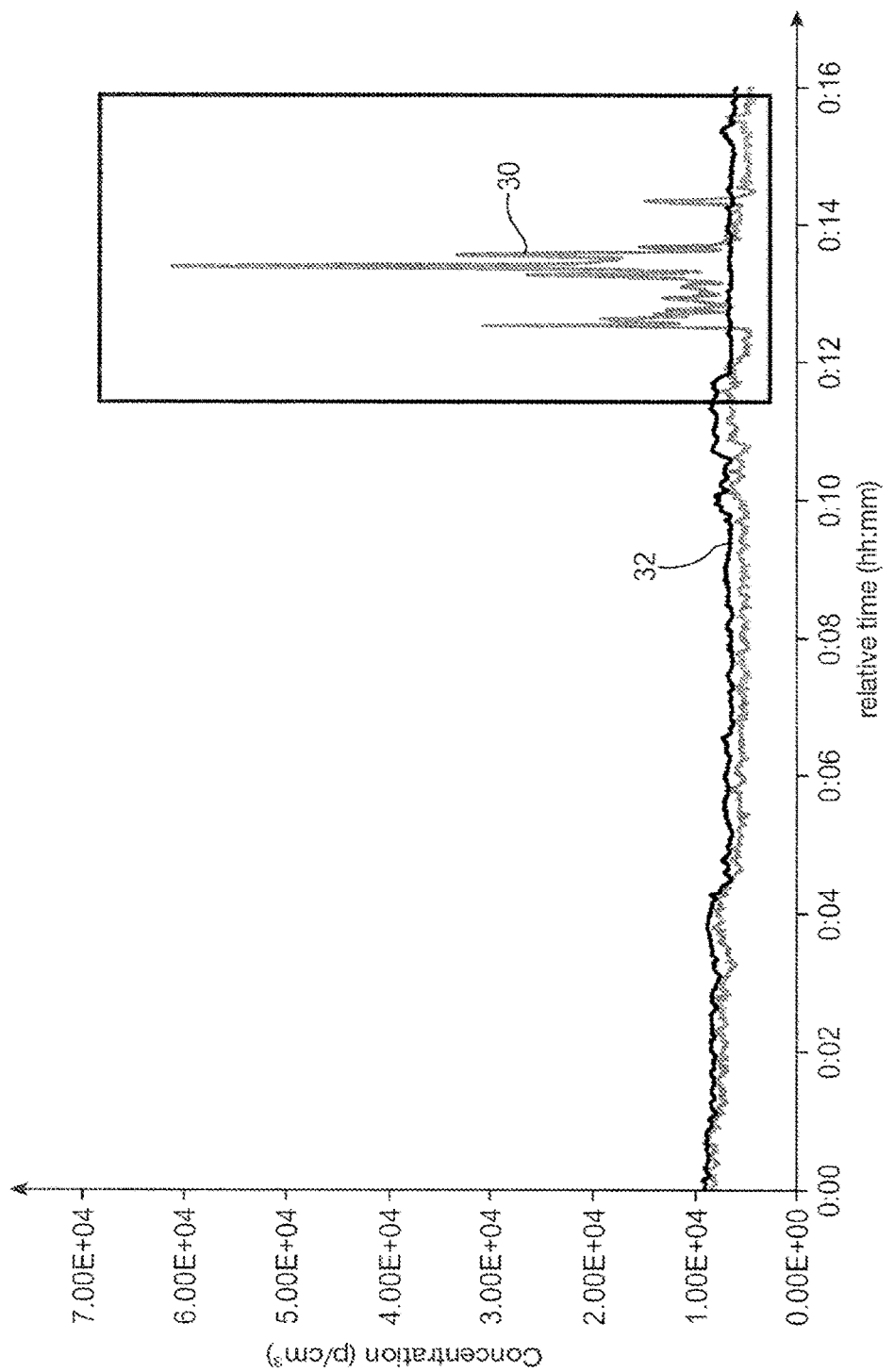
FIG. 6 shows measurements of particle concentrations in the presence of SiC nanoparticles of interest carried out by the particle detection system according to this invention.
Figure 7:
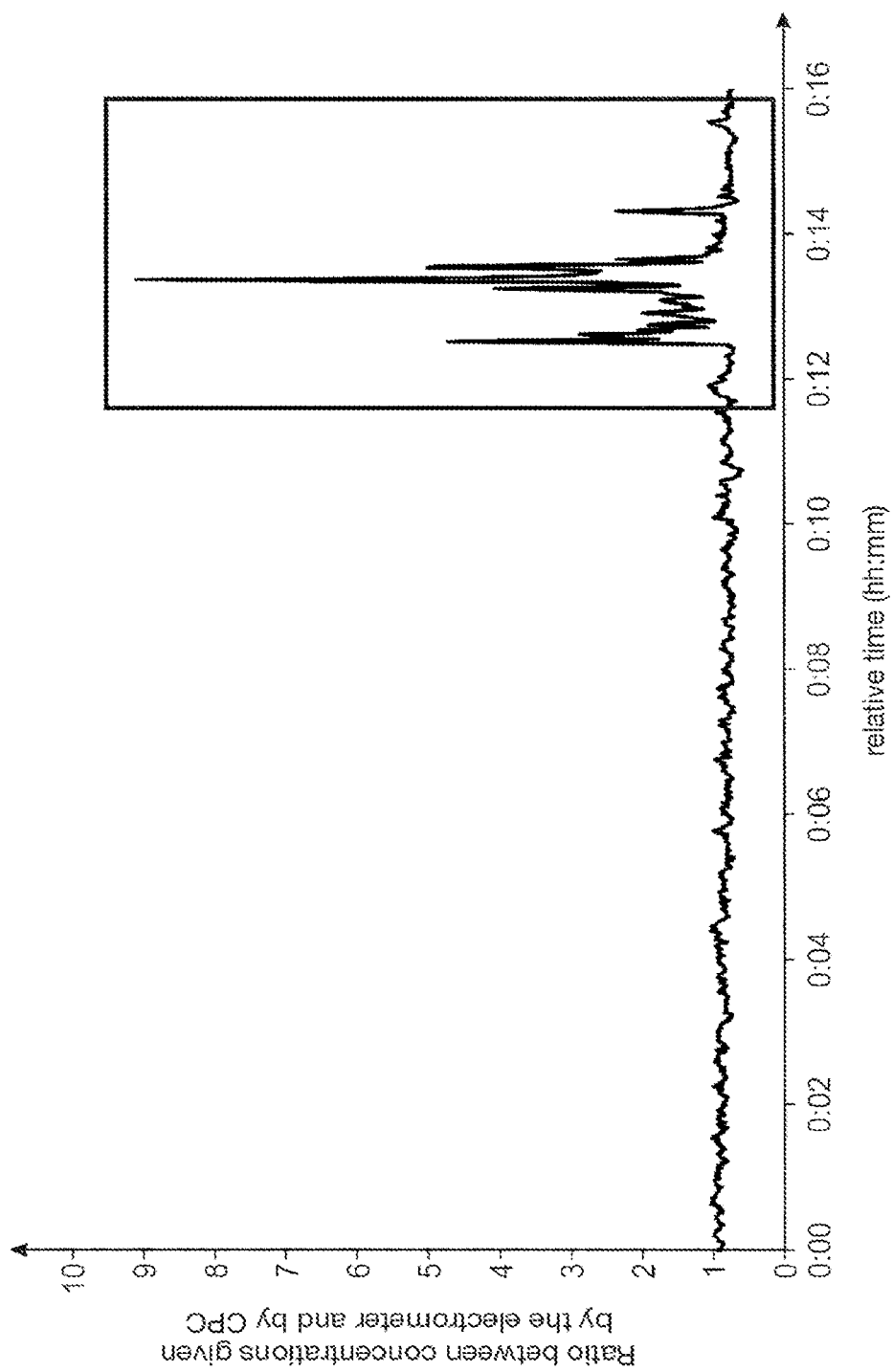
FIG. 7 shows the variation in the ratio between measurements of particle concentrations in the presence of SiC nanoparticles of interest calculated by the particle detection system according to this invention.

FIG. 6 shows the variation in particle concentrations (as a number of particles/cm3) obtained with the first device 110 (curve 30) and with the second device 112 (curve 32), over a 16-minute period, during a measurement of the concentration of particles in an air flow that comprises SiC nanoparticles, in addition to the particles in ambient air. These measurements are carried out during two phases: a first phase corresponding to the first 12 minutes during which the SiC particles are not manipulated (that does not generate an SiC aerosol in the air flow), and a second phase from the 12th minute to the 16th minute during which SiC particles are manipulated that does generate SiC aerosols in the air flow. FIG. 7 shows the variation of the ratio between these measurements that is calculated by the calculation unit 118. The ratio of concentrations is close to 1 as long as SiC particles are not manipulated and therefore there are no SiC aerosols in the air flow, as for the measurements described above with reference to FIGS. 2 and 3. As soon as SiC particles are manipulated, thus generating SiC aerosols in the air flow, the first device 110 strongly overestimates the concentration of particles in the air flow relative to the second device 112 due to the aggregates and/or clusters of SiC particles that form. The ratio of the measured concentrations quickly reaches 10 due to the fact that the second device 112 does not detect a significant change in the concentration, while the first device 110 overestimates the number of SiC particles in the air flow.

Figure 8:
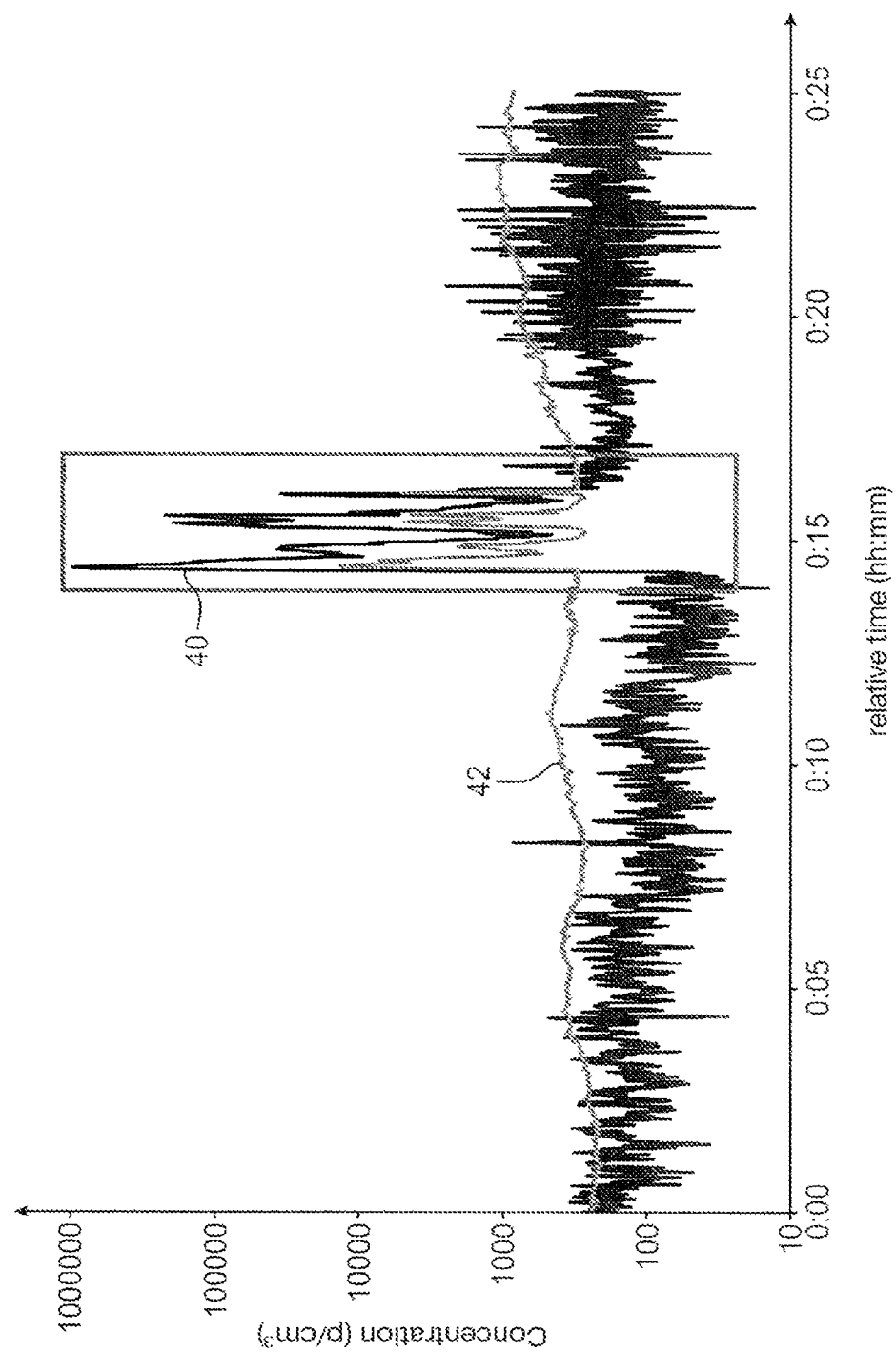
FIG. 8 shows measurements of particle concentrations in the presence of carbon black nanoparticles of interest carried out by the particle detection system according to this invention.
Figure 9:
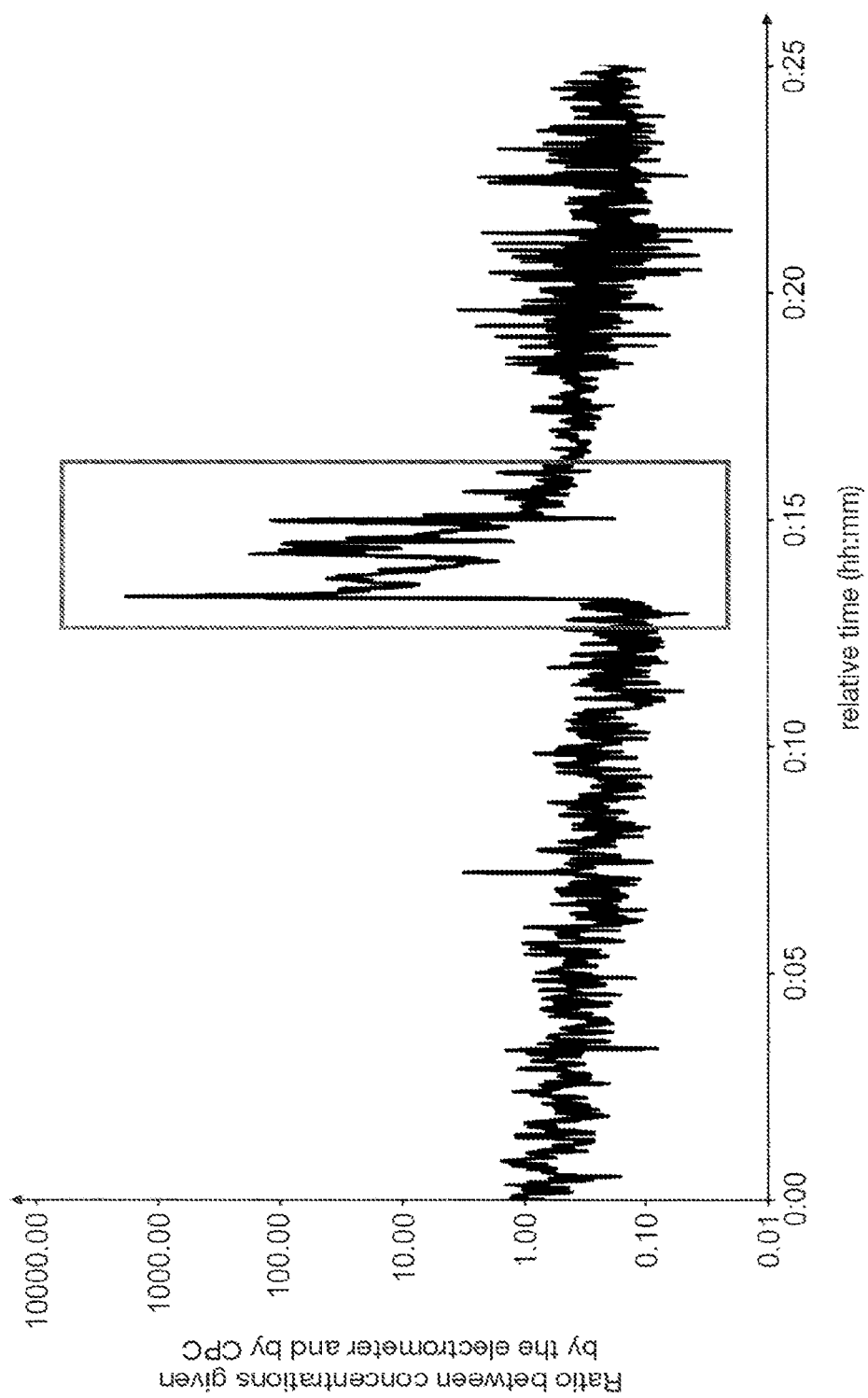
FIG. 9 shows the variation in the ratio between measurements of particle concentrations in the presence of carbon black nanoparticles of interest calculated by the particle detection system according to this invention, and FIG. 10 diagrammatically shows a particle detection system according to a second embodiment of this invention.

FIG. 8 shows the variation in particle concentrations (as a number of particles/cm$^3$) obtained with the first device 110 (curve 40) and with the second device 112 (curve 42), over a 25-minute period, during a measurement of the concentration of particles in an air flow that comprises carbon black nanoparticles, in addition to the particles in ambient air. These measurements are carried out in three phases: a first phase corresponding to the first 14 minutes during which the carbon black particles are not manipulated (in which no carbon black aerosol is generated in the air flow), a second phase from the $14^{th}$ minute to the $17^{th}$ minute during which carbon black particles are manipulated and in which carbon black particles aerosols are generated in the air flow, and a third phase from the $17^{th}$ minute to the $25^{th}$ minute during which carbon black particles are no longer manipulated. FIG. 9 shows the variation of the ratio between these measurements that is calculated by the calculation unit 118. The ratio of the concentrations is close to 1 and is globally less than 1 as long as carbon black particles are not being manipulated and therefore there are no carbon black aerosols in the air flow. In this case, a higher variability of this ratio is obtained during this first phase due to the low concentrations of particles in ambient air (fewer than 1000 particles/cm$^3$), the measurement carried out by the first device 110 not being very precise for such concentrations. As soon as carbon black particles are manipulated, thus generating carbon black aerosols in the air flow, the first device 110 strongly overestimates the concentration of particles in the air flow relative to the second device 112 due to the aggregates and/or clusters of carbon black particles that form. The ratio of the measured concentrations then quickly exceeds 1000.

Therefore the system 100 can specifically demonstrate the presence of an aerosol of interest other than particles of the ambient air, very significantly and with a response time of the order of one second. For example, the presence of particles of interest is determined by the calculation unit 118 when the calculated value of the ratio between the measurements provided by devices 110, 112 exceeds a threshold value, the value of this threshold depending on elements making up the system 100 and for example determined in advance during a calibration phase of the system 100.

Furthermore, even in the presence of large variations in the concentrations of particles in ambient air, since the concentrations measured by the two devices 110, 112 vary in almost the same way following these variations, the ratio between the two measurements is not affected by these variations and always signals the presence of these particles of interest The system 100 also comprises a processing unit 120 receiving the signal output by the calculation unit 118 as input, in other words the ratio and/or the difference between the values of particle concentrations output by the two measurement devices 110, 112, and using this signal to perform one or several required functions. It is possible that units 118 and 120 are the same element. For example, the processing unit 120 can trigger an alarm (visual, sound, etc.) when the value of the ratio and/or the difference between the concentration measurements carried out by the devices 110, 112 exceeds a given threshold. The processing unit 120 can also control a method as a function of the value of this ratio and/or this difference, and for example trigger a shutdown, a regulation or start up any type of action for example related to a manufacturing or other type of process. The processing unit 120 can also record a signal output by the calculation unit 118. The processing unit 120 can also perform other functions or processing of the signal output by the calculation unit 118.

Figure 10:
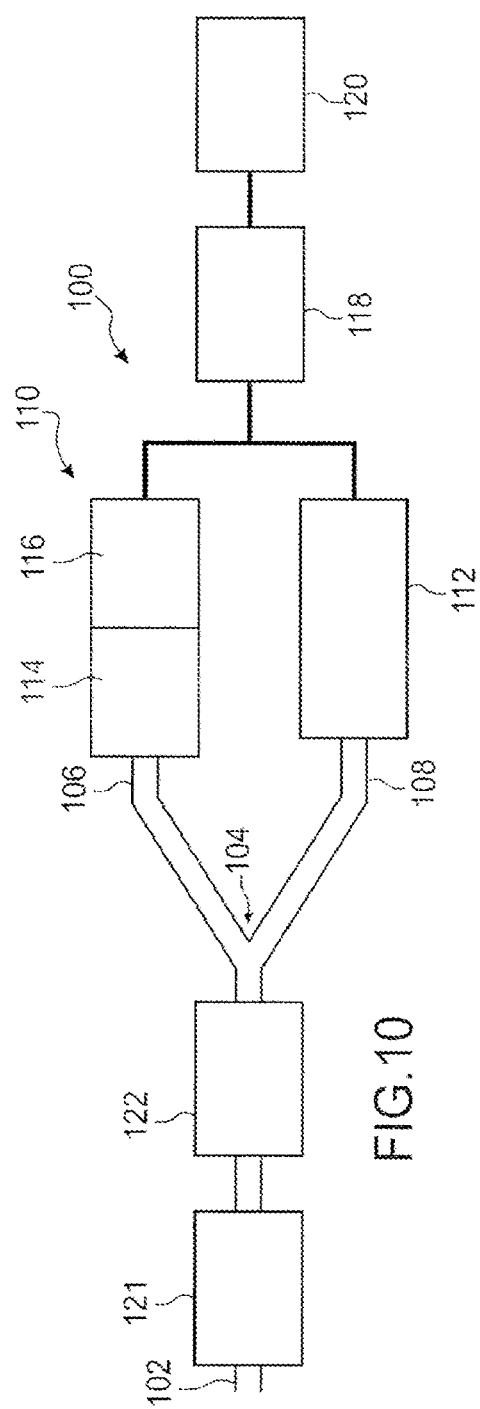

FIG. 10 diagrammatically shows a second embodiment of the system 100.

Unlike the first embodiment described above with reference to FIG. 1, a charger or neutraliser 121 of particle electrical charges is placed upstream from the flow separator 104 and is coupled to a particle selection device 122 that is capable of selecting at least a fraction of the particles in the air flow as a function of their behaviour (electrical mobility and/or aerodynamic mobility and/or size), for example corresponding to a Differential Mobility Analyser (DMA) and its control system. Thus, air flow particles circulating in the inlet channel 102 are electrically charged or neutralised by the charger or the neutraliser 121, and the device 122 then makes a selection of particles as a function of their behaviour, for example as a function of their size. Only particles for which the size lies within the required range are kept by the device 122 and sent to the flow separator 104. Particle concentrations are then measured by the devices 110 and 112, as described above.

As a variant, in the system 100 according to this second embodiment, the device 122 may be capable of selecting particles as a function of their electrical behaviour (electrical mobility) or their aerodynamic behaviour (aerodynamic mobility) and thus select particles by their size without these particles being electrically charged or neutralised, for example when the device 122 is a cyclone.

According to another variant embodiment, a selection according to the size of the particles may be carried out directly at the first device 110 that may be capable of counting only particles with a given size or for which the size lies within a selected range.

According to another variant, the first device 110 and/or the second device 112 may be capable of measuring the concentration as a number of particles and also making this measurement for several ranges of particles sizes.

Regardless of which embodiment or variant is considered, the system 100 may comprise a third device in parallel to the measurement devices 110, 112 to determine the nature (inorganic or organic) of the characterised aerosol. In this case, the flow separator 104 can separate the inlet air flow into three distinct air flows instead of two distinct flows, so that this third device can determine the nature of the particles at the same time as measurements are carried out by the devices 110, 112.

Furthermore, for the different embodiments and variants described above, the first device 110 can comprise an optical particle counter (OPC) instead of the electrometer measuring device 116 coupled to the charger 114. In particular, such an optical particle counter can estimate the number and mass of the particles. For example, such an optical particle generator corresponds to the equipment proposed by the GRIMM manufacturer under its trade name "Dustmonitor 1.109" or to the commercial equipment proposed by the PALLAS manufacturer under the trade name FIDAS.

The calculation unit 118 can also use the measurement results provided by the devices 110 and 112 to calculate a particle concentration value. A prior calibration or model of the system 100 is carried out for this purpose before the measurements so that the calculation of the value of the particle concentration can be made from measurements carried out by the devices 110 and 112.

For example, such a system 100 is adapted to:
detect that a nanostructured aerosol is accidentally put into suspension to give an alert about potential exposure of persons to this aerosol,
monitor a method involving nanostructured aerosols,
slave a method involving nanostructured aerosols,
record measured and calculated data, and
detect an emission of a nanostructured aerosol into the environment.

In the above description, an air flow containing particles to be detected is formed because measurement devices collect this air by suction. This air can be derived from an air flow sent to the detection system, but this air can also be collected by the detection system from an air volume that does not form part of an air flow, in other words that is not circulating, for example that is contained in a closed containment.

The invention claimed is:

1. A system for detecting particles in air, comprising:
a first particle concentration measurement device comprising at least one of an electrometer measuring device, coupled to a charger, or an optical particle counter;
a second particle concentration measurement device comprising at least one condensation particle counter;
a calculation unit configured to calculate at least one of a ratio and a difference between a first measurement of the particle concentration in an airflow, to be performed by the first particle concentration measurement device, and a second measurement of the particle concentration in the airflow, to be performed by the second particle concentration measurement device, and configured to make a comparison between the at least one of the ratio and the difference between the first and second measurements of particle concentrations in the air flow and a threshold value to determine presence of particles of interest other than ambient air particles.

2. A system according to claim 1, further comprising a flow separator comprising an inlet into which the air flow is to be directed and two outlets coupled to inlets to the first and second particle concentration measurement devices.

3. A system according to claim 2, further comprising a particle selection device located upstream from the flow separator and configured to select at least some of the particles in the air flow depending on their behavior such that the air flow received by the first and second particle concentration measurement devices contains only the selected particles.

4. A system according to claim 3, wherein the particle selection device comprises a cyclone, or wherein the particle selection device comprises an electrical mobility differential analyzer coupled to a charger or a neutralizer of electrical charges of particles in the air flow.

5. A system according to claim 1, further comprising a processing unit of the signal output by the calculation unit.

6. A system according to claim 1, further comprising a device configured to determine a nature of particles in the air flow.

7. A system according to claim 1, wherein the calculation unit is configured to calculate a concentration of particles of interest contained in the air flow and distinct from particles in ambient air.

8. A system according to claim 1, wherein the calculation unit is configured to compare the at least one of the ratio and the difference to a threshold value determined from a difference in particle measurement characteristics of the first and second particle concentration measurement devices.

9. A system according to claim 1, wherein the calculation unit is configured to compare the at least one of the ratio and the difference to a threshold value determined from an overestimation of a concentration of the particles of interest in the air flow measured by one of the first and second particle concentration measurement devices.

10. A system according to claim 1, wherein the threshold value is determined in advance during a calibration phase of the system.

11. A method of detecting particles in air comprising:
a first measurement of a concentration of particles in an air flow by a first particle concentration measurement device comprising at least one of an electrometer measuring device, coupled to a charger, or an optical particle counter;
a second measurement of a concentration of particles in the air flow by a second particle concentration measurement device comprising at least one condensation particle counter;
calculating at least one of a ratio and a difference between the first and the second measurements of the particle concentration in the air flow;
comparing between the at least one of the ratio and the difference between the first and second measurements of the concentration of particles and a threshold value used to determine presence of particles of interest other than those in ambient air.

12. A method according to claim 11, further comprising, before the first and second particle concentration measurements, selecting at least some of the particles in the air flow as a function of their behavior, such that the first and second particle concentration measurements are carried out from the air flow that contains only the selected particles.

13. A method according to claim 11, further comprising determining a nature of particles in the air flow.

14. A method according to claim 11, further comprising calculating a concentration of particles of interest contained in the air flow and distinct from particles in ambient air.

15. A method according to claim 11, wherein the airflow contains ambient particles and particles of interest, the method comprising:
the first measurement of a first concentration of both of the ambient particles and particles of interest in the airflow;
the second measurement of a second concentration of both of the ambient particles and the particles of interest in the airflow;
calculating at least one of a ratio and a difference between the first and the second concentrations; and
comparing the at least one of the ratio and the difference to a threshold value to determine the presence of the particles of interest in the airflow.

16. A method according to claim 11, comprising comparing the at least one of the ratio and the difference to a threshold value determined from a difference in particle measurement characteristics of the first and second particle concentration measurement devices.

17. A method according to claim 11, comprising comparing the at least one of the ratio and the difference to a threshold value determined from an overestimation of a concentration of the particles of interest in the air flow measured by one of the first and second particle concentration measurement devices.

18. A method according to claim 11, wherein the threshold value is determined in advance during a calibration phase.

19. A method of detecting particles in air comprising:
   performing a first measurement of a concentration of particles in a first sample of ambient air containing ambient particles and particles of interest by a first particle concentration measurement device comprising at least one of an electrometer measuring device, coupled to a charger, or an optical particle counter;
   performing a second measurement of a concentration of particles in a second sample of the ambient air by a second particle concentration measurement device comprising at least one condensation particle counter;
   calculating at least one of a ratio and a difference between the first and the second measurements; and
   comparing the at least one of the ratio and the difference between the first and second measurements of the concentration of particles to a threshold value to detect a presence of the particles of interest other than the ambient particles in the ambient air.

20. A method according to claim 19, wherein the threshold value is determined from a difference in particle measurement characteristics of the first and second particle concentration measurement devices.

21. A method according to claim 19, wherein the threshold value is determined from an overestimation of a concentration of the particles of interest in the ambient air measured by one of the first and second particle concentration measurement devices.

* * * * *